United States Patent [19]

Cowley et al.

[11] Patent Number: 5,243,083
[45] Date of Patent: Sep. 7, 1993

[54] THERMOSYPHONIC REACTION OF OXYGEN WITH ISOBUTANE AND REACTOR

[75] Inventors: Roderick S. Cowley, Den Haag, Netherlands; Darrell D. Kinzler, Framingham, Mass.

[73] Assignee: Texaco Chemical Company, White Plains, N.Y.

[21] Appl. No.: 918,107

[22] Filed: Jul. 24, 1992

[51] Int. Cl.$^5$ .......................................... C07C 409/04
[52] U.S. Cl. .................................. 568/571; 568/577
[58] Field of Search ............... 568/569, 571, 572, 573, 568/910, 577

[56] References Cited

U.S. PATENT DOCUMENTS

| | | | |
|---|---|---|---|
| 2,845,461 | 7/1958 | Winkler | 568/571 |
| 3,825,605 | 7/1974 | Johnston | 568/910 |
| 3,907,902 | 9/1975 | Grane | 568/571 |
| 4,294,999 | 10/1981 | Grane et al. | 568/910 |
| 4,296,262 | 10/1981 | Grane et al. | 568/910 |
| 4,296,263 | 10/1981 | Worrel et al. | 568/910 |
| 4,404,406 | 9/1983 | Lutz et al. | 568/571 |
| 4,408,081 | 10/1983 | Foster et al. | 568/571 |
| 4,801,755 | 1/1989 | Sanderson et al. | 568/571 |

FOREIGN PATENT DOCUMENTS 312846 10/1971 U.S.S.R. ............................. 568/573

*Primary Examiner*—Werren B. Lone
*Attorney, Agent, or Firm*—Jack H. Park; Kenneth R. Priem; Carl G. Ries

[57] ABSTRACT

A method and apparatus for continuously conducting an exothermic chemical reaction between a reactant feedstock such as isobutane and a chemical reactant such as oxygen wherein a circulating stream of the reaction mixture continuously flows up an upstanding draft tube coaxially mounted in a closed upstanding cylindrical reactor and then down the annulus between the cylindrical reactor and the draft tube to establish circulatory motion, and wherein the circulatory motion is thermosyphonically maintained by charging oxygen adjacent the bottom of the draft tube for exothermal reaction with isobutane in the draft tube to thereby heat the upflowing circulating stream, wherein a stream of cold isobutane is continuously introduced adjacent the top of the annulus to cool the circulating stream by direct heat exchange contact, wherein indirect heat exchange cooling coils are provided in the annulus adjacent the top thereof for further cooling the downflowing circulating stream and wherein a discharge line is provided at the top of the reactor for continuously removing a discharge stream from the reactor.

5 Claims, 1 Drawing Sheet

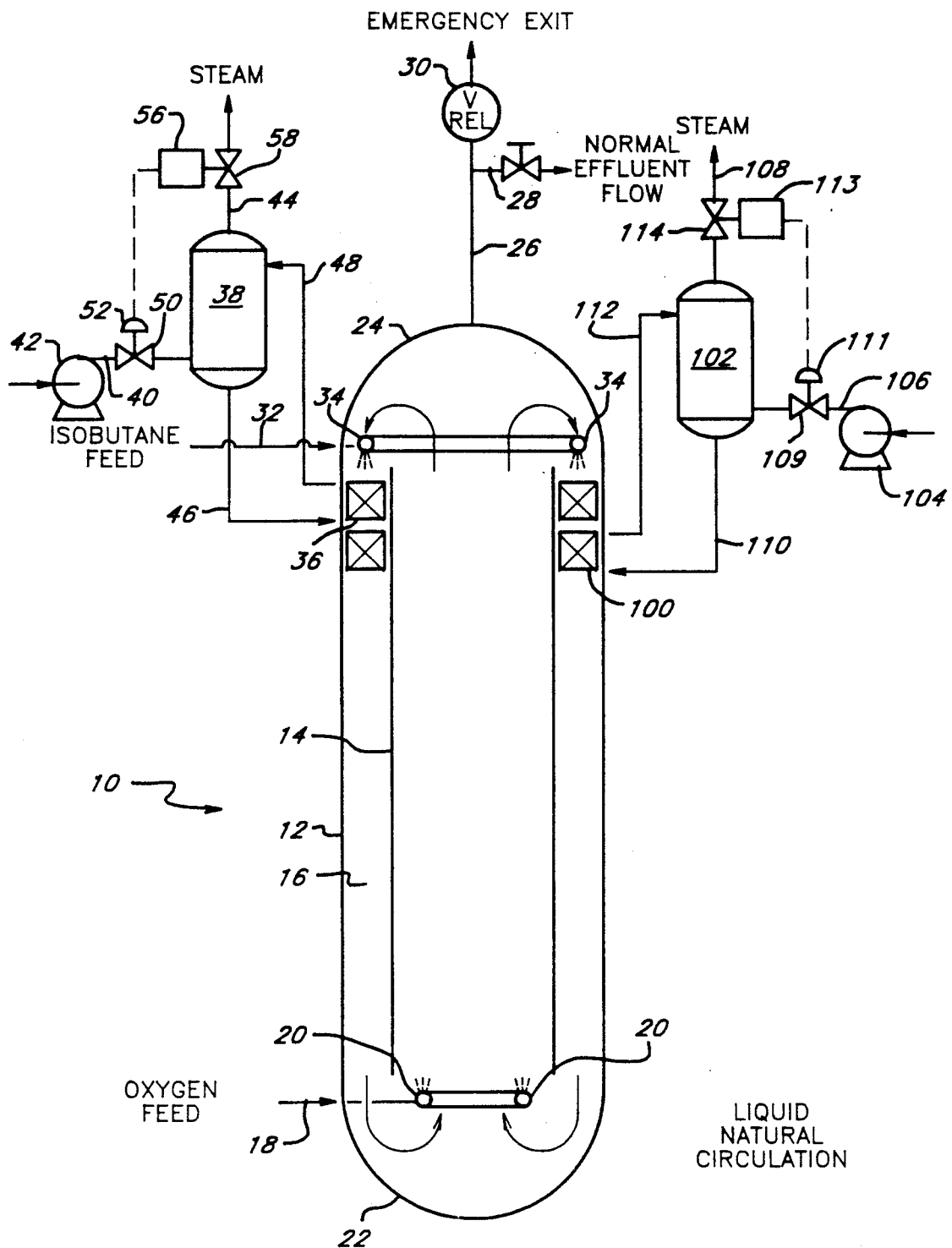

THERMOSYPHONIC REACTION OF OXYGEN WITH ISOBUTANE AND REACTOR

BACKGROUND OF THE INVENTION

1. Technical Field of the Invention

This invention relates to a thermosyphonic liquid phase method for reacting oxygen with isobutane to provide a solution comprising unreacted isobutane, tertiary butyl hydroperoxide, tertiary butyl alcohol and by-products and to a thermosyphonic reactor useful for the process.

2. Prior Art

Grane U.S. Pat. No. 3,907,902 is directed to a method for increasing the selectivity for tertiary butyl hydroperoxide during the liquid phase oxidation of isobutane with molecular oxygen by introducing a small amount of isopropyl alcohol or secondary butyl alcohol or isobutyl alcohol into the reaction zone.

Lutz et al. U.S. Pat. No. 4,404,406 is directed to a method for the preparation of tertiary butyl hydroperoxide by the direct oxidation of isobutane with oxygen wherein the oxidation is conducted in a dense super critical phase reaction mixture at a temperature in excess of the critical temperature of the mixture and at a pressure in excess of the critical pressure of the mixture.

Jubin U.S. Pat. No. 4,128,587 is directed to a method for regulating the conversion and selectivity obtained in oxidizing isobutane with molecular oxygen by regulating the concentration of tertiary butyl alcohol in an isobutane feed stream.

It is also known to promote the reaction of oxygen with isobutane or cumene by the use of a catalyst.

For example, Joris U.S. Pat. No. 2,577,768 is directed to the liquid phase oxidation of cumene with elemental oxygen in the presence of sodium bicarbonate. Johnston U.S. Pat. No. 3,825,605 is directed to the oxidation of isobutane to tertiary butyl alcohol and other by-products in the presence of a metal acetate catalyst. The use of sodium fluoride as a catalyst to promote the oxidation of cumene with molecular oxygen is disclosed in McAvoy U.S. Pat. No. 3,833,663. Barone in U.S. Pat. No. 4,152,358 discloses that metal phosphate catalysts can be used to promote the Oxidation of tertiary, arryl or cycloalkanes.

Grane et al. U.S. Pat. No. 4,294,999 discloses a method for the preparation of tertiary butyl alcohol by the oxidation of isobutane with molecular oxygen in the presence of a molybdenum catalyst. In U.S. Pat. No. 4,296,262, Grane et al. also disclose the use of molybdenum catalysts to promote the reaction of isobutane with molecular oxygen.

Worrell U.S. Pat. No. 4,296,263 is directed to a method for reacting a crude feed mixture of n-butane and isobutane with molecular oxygen in the presence of a catalyst.

It is also known to conduct gas-liquid chemical reactions in "closed loop" reactors as disclosed, for example, in Papp et al. U.S. Pat. No. 4,312,837 which discloses the use of a closed loop reactor comprising an ascending vertical tube and a descending vertical tube for the reaction of synthesis gas with an olefin in the presence of a catalyst. A reaction of this nature is also known as an Oxo synthesis.

Other references showing closed loop gas-liquid chemical reactors include Westerlund U.S. Pat. No. 3,502,443 which discloses a reactor useful for chlorine dioxide generation, Schuster et al. U.S. Pat. No. 4,482,692 which discloses a gas-liquid reaction conducted in a closed loop such as an oxygenation reaction. Other reactors are shown in Prave et al. U.S. Pat. Nos. 4,545,945 and 4,683,122 wherein a gas and a liquid are brought into contact in a dual zone reactor having an upflow portion and a downflow portion.

Vernon U.S. Pat. No. 3,212,860 discloses a process wherein two immiscible liquid chemicals are reacted in an upstanding reactor having a downflow portion and an upflow portion, such as an alkylation reaction wherein an olefin and isobutane are reacted.

SUMMARY OF THE INVENTION

In accordance with the present invention a closed loop-type reactor is disclosed which is useful for the thermosyphonic liquid phase exothermic reaction of two or more chemicals, such as the liquid phase exothermic reaction of isobutane with molecular oxygen in an upstanding reactor. The reactor comprises an upstanding upflow section and an upstanding downflow section, The downflow section containing an indirect heat exchange segment comprising, for example, a plurality of heat exchange coils mounted in the downflow section and fluidly interconnected with a source of a coolant which is positioned adjacent to, but above the cooling coils so that a heat exchange fluid, such as water, will create a thermosyphonic countercurrent flow through the heat exchange coil with or without vaporization and without a need for pumps or other moving parts. One or more inlet lines for fresh feed to the thermosyphonic reactor are provided adjacent the top of the downflow section and an outlet line is provided in the upper lateral leg.

In accordance with the method of the present invention an isobutane feed line is provided adjacent the top of the downflow section of the reactor so that a comparatively cold stream of fresh isobutane feedstock can be charged to the reactor to mix with the downflowing stream of reaction mixture, to thereby define an isobutane injection zone. The reaction mixture is further cooled in the downflowing section by indirect heat exchange contact with a cooling fluid adjacent the upper end of the downflow segment. As a consequence, the temperature of the reaction mixture will be lowered and the density of the reaction mixture will increase to thereby induce downward flow of the reaction mixture through the downflow segment. At the bottom of the reactor the direction of flow reverses and the reaction mixture starts to flow in an upward direction to the upward section. In accordance with the present invention an inlet line, such as a sparger, is provided for introducing oxygen into the reaction mixture adjacent the bottom of the upflow section for reaction with the isobutane in the reaction mixture to form additional quantities of tertiary butyl hydroperoxide and tertrary butyl alcohol, to thereby define an injection zone. As the reaction mixture flows through the upflow segment the temperature of the reaction mixture progressively increases thus progressively decreasing its density and inducing upward flow through the upflow section. At the top of the reactor and above the upflow section a stream of reaction mixture is removed, the amount removed being such that the reactor is at all times full of liquid. This is important because if there is a vapor space at the top of the reactor, a potentially explosive mixture of vapors could accumulate.

BACKGROUND OF THE INVENTION

In conducting an oxidation reaction such as one wherein molecular oxygen is reacted with isobutane to provide tertiary butyl hydroperoxide and additional tertiary butyl alcohol, the reaction proceeds with the liberation of a significant amount of heat.

Because the chemical reaction takes place in the liquid phase, it is conventional to provide a continuous stirred reactor such as an autoclave which is provided with a jacket for the circulation of a heat exchange fluid and with a mechanical device such as an impeller for thoroughly stirring the contents of the autoclave. Although this arrangement permits heat recovery from the heat exchange fluid, the process is made more hazardous because it is necessary to provide flanged openings and seals such as shaft seals.

In order to improve the safety of the process, to provide for more efficient mixing of the reactants, to provide for efficient recovery of the heat generated by the chemical reaction for use elsewhere in the plant, the process of the present invention is conducted in a closed loop reactor uniquely designed so that there is no need to utilize shaft seals or moving parts or electrically powered equipment which can generate sparks and which relies upon a secure power supply.

BRIEF DESCRIPTION OF THE INVENTION

In one aspect, the process of the present invention comprises a method for continuously exothermally reacting molecular oxygen with isobutane to form tertiary butyl hydroperoxide, tertiary butyl alcohol and by-products by thermosyphonically circulating a reaction mixture stream comprising isobutane, which contains tertiary butyl hydroperoxide, tertiary butyl alcohol and reaction by-products around an upright thermosyphonic reactor comprising an upflow section and a downflow section, continuously cooling the reaction mixture (e.g., by removing heat from the circulating stream in a heat exchange zone adjacent the top of the downflow section by continuously flowing the circulating stream of reaction mixture downwardly through the downflow section and upwardly through an upflow section). The temperature of the reaction mixture is progressively increased in the upflow section (e.g., oxygen is added at the bottom of the upflow section and reacts with the isobutane and progressively increases the temperature). A product stream is withdrawn at the top of the reaction in an amount sufficient to maintain a predetermined volume of reaction mixture in the reactor, whereby the density of the reaction mixture in the downflow section will be greater than the density of the reaction mixture in the upflow section whereby continuous thermosyphonic circulation can be maintained and continuous mixing of the feed stream with the reaction mixture can be accomplished without the use of externally driven mixers and circulators.

In accordance with a preferred aspect of the present invention, the thermosyphonic reactor comprises an upstanding closed cylindrical reactor adapted to be filled with a circulating stream of reaction mixture. An upstanding draft tube is mounted coaxially inside of the cylindrical reactor and annularly spaced from the cylindrical side of the reactor. An inlet line comprising sparging means is mounted in the reactor adjacent the bottom of the draft tube for charging oxygen therethrough for exothermic reaction with isobutane in the flowing stream of reaction mixture to thereby heat the flowing reaction stream of reaction mixture as it flows upwardly through the draft tube, thus defining an oxygen injection zone. Sparging means are also mounted in the reactor adjacent the top of the annular space between the cylinder wall of the reactor and the draft tube for introducing comparatively cool fresh isobutane feedstock to the reactor. Indirect heat exchange means comprising a plurality of heat exchange coils are mounted in the annular space adjacent the top thereof for cooling the circulating stream of reaction mixture to thereby provide an isobutane injection zone and to provide for a density differential between the portion of the reaction mixture flowing downwardly through the annular space and the portion of the reaction mixture flowing upwardly through the draft tube. Again, a discharge line is provided adjacent the top of the cylindrical reactor for removing a stream of reaction mixture in a volume equivalent to the volume of fresh isobutane feedstock charged to the reactor.

In the preferred embodiment of the invention, the cooling means comprises a steam release drum positioned adjacent to and above the cooling coils in the annular space. A charge line is provided for delivering a stream of comparatively cool cooling water to the steam drum and a water line is provided adjacent the bottom of the steam drum and interconnected with the bottom of the cooling coils in the annular space so that cooling water can be charged to the bottom of the coils mounted in the annular space. The water will be heated in the cooling coils and at least a portion of the water will normally be converted to steam. A steam line interconnects the top of the cooling coils and leads to a point adjacent the top of the steam release drum. A steam discharge line is mounted adjacent the top of the steam drum for removing steam therefrom. As a consequence, the cooling water, being denser than steam, will thermosyphonically flow from the steam drum to the cooling coils where it will be heated to provide hot water and steam which will thermosyphonically flow back to the steam drum. The steam is removed overhead for use elsewhere in the plant. In accordance with this preferred embodiment, a pressure control valve is mounted in the steam discharge line to control the rate at which steam is released from the steam drum. A flow control valve is mounted in the water charge line and functionally working with the pressure control valve for regulating the rate at which water is charged to the steam drum to a rate consistent with the rate at which steam is released from the drum and maintaining thermal equilibrium. The rate at which cool water is charged to the indirect heat exchange coils through the cool water charge line, as a consequence, the rate of cooling of the flowing stream of reaction mixture by the heat exchange coils and, hence, the temperature at which the chemical reactants flow from the heat exchange coils adjusts itself by thermosyphonic action and generates the steam released through the steam discharge line. Thereby a density differential is automatically maintained between the portion of the circulating reaction mixture flowing downwardly through the annular space and the portion of the circulating reaction mixture flowing upwardly through the draft tube to thereby ensure that thermosyphonic flow of the reactants around the thermosyphonic reactor is automatically maintained.

If desired, and as a safety precaution, two separate banks of cooling coils mounted in series in the annular space may be provided which operate identically and in a manner described above as an added safety measure so that if one of the cooling coils should fail, the other will remain in operation. Also, an emergency exit or blowout or rupture disc can be provided at the top of the reactor so that, in the case of an excessive buildup of pressure in the reactor, the rupture disc will fail and permit the reaction mixture to blow from the reactor without causing an explosion.

DESCRIPTION OF THE DRAWING

The drawing is a schematic side elevation view showing, schematically, the manner in which the thermosyphonic reactor of the present invention and the cooling means for the endothermic reactor segment are assembled and operated.

DETAILED DESCRIPTION OF THE PREFERRED EMBODIMENT

Turning now to the drawing, there is schematically shown a preferred embodiment of the thermosyphonic reactor of the present invention designated generally by the numeral 10. The thermosyphonic reactor 10 comprises an upstanding cylindrical shell 12 in which a draft tube 14 is coaxially mounted, the draft tube having a diameter such that an annular space 16 is provided between the inner wall of the shell 12 and the draft tube 14.

An oxygen inlet line 18 provided with suitable means such as spargers 20-20 is provided for introducing oxygen into a circulating stream of reaction mixture flowing downwardly through the annular space 16 and upwardly through the draft tube 14. The bottom of the reactor is closed by a lower cap 22 and the top of the reactor is closed by an upper cap 24.

An outlet line 26 is provided at the top of the upper cap 24 provided with a normal discharge branch line 28 and a rupture disc 30.

An isobutane feed line 32 provided with suitable inlet means such as sparging nozzles 34-34 is provided for introducing comparatively cool fresh isobutane feedstock into the circulating stream of reaction mixture in an amount equivalent to the amount of reaction mixture withdrawn through the line 26.

At least one bank of cooling coils 36 are mounted adjacent the top of the annular space 16 for further cooling the portion of the reaction mixture flowing downwardly through the annular space 16.

In accordance with this embodiment a steam discharge drum 38 is provided which is mounted adjacent to and above the cooling coil 36. Comparatively cool cooling water or other suitable fluid is charged to the drum 38 by way of a charge line 40 leading from a pump 42.

A steam discharge line 44 is provided for removing steam overhead from the steam drum.

A water line 46 leads from the bottom of the drum 38 to the bottom of the cooling coils 36 and a steam line 48 for recycling hot water and steam is provided which leads from the top of the cooling coil 36 to a point adjacent the top of the steam drum 38.

In accordance with this embodiment a flow control valve 50 is provided in the feed line 40 for the steam drum 38 which is operatively connected with a pressure control valve with the actuating means. The flow control means 52 for the flow control 50 is operatively interconnected with the control means 56 for a pressure control valve 58 mounted in the steam discharge line 44.

In accordance with the preferred embodiment of the present invention, at least two banks of cooling coils are provided, the second bank of cooling coils 100 being mounted adjacent to the first bank of cooling coils 36 in series therewith and interconnected with a steam discharge drum 102 mounted adjacent to and above the cooling coils 100. Again, comparatively cool cooling fluid such as water is charged to the drum 102 from a pump 104 through a line 106 and steam is withdrawn from the drum 102 by way of a steam discharge line 108. Cool cooling water flows from the bottom of the drum 102 to the cooling coils 100 through a water discharge line 110 and hot water and steam return to the steam discharge drum 102 by way of a steam line 112. Again, the rate at which water is charged to the drum 102 by the charge line 106 is controlled by a valve 110, the actuating control means 113 of which is operatively connected with the control means 113 for a pressure control valve 114 mounted in the steam discharge line 108.

OPERATION

In accordance with the present invention, a thermosyphonic reactor such as the reactor 10 shown in the drawing is filled with isobutane and oxygen charged to the reactor by way of the oxygen charge line 18 while fresh isobutane feedstock is charged to the reactor by way of the feed line 32.

The oxygen sparged into the circulating stream of reaction mixture through the spargers 20-20 reacts with the isobutane as the reaction mixture flows up the draft tube 14 thereby progressively increasing the temperature of the reaction mixture. At the top of the draft tube 14, a stream of reaction mixture is withdrawn through the line 26 and an equivalent amount of liquid is replaced in the form of fresh isobutane feedstocks with the charge line 32 in spargers 34-34.

Both the fresh isobutane feedstock and cooling coils mounted in the annular space 16 will cool the reaction mixture at the top of the annular space 16. As a consequence the temperature will decrease and the density will increase as compared with the temperature and density of the reaction mixture at the top of the draft tube 14. This will induce thermosyphonic downward flow through the annular space 16 and upwardly through the draft tube 14 without the use of agitators, pumps or other external means.

This equipment mediates the partial oxidation of isobutane the liquid phase to tertiary butyl hydroperoxide and tertiary butyl alcohol. The reaction proceeds slowly without the aid of homogeneous or heterogeneous catalysts, but it is autocatalytic, which is to say that the presence of the product tertiary butyl hydroperoxide greatly accelerates the rate of hydrocarbon conversion. The reactions take place with equal facility in the liquid or vapor phase. In either case, high pressure is required: for liquid operation the pressure is required to prevent vaporization, and for vapor phase operation the pressure is required to densify the reacting mixture reactions are highly exothermic. About 25% of the feed isobutane is converted in one pass through the reactor.

Because the reaction is autocatalytic a backmixed reactor is preferred rather than a plug flow design. Among the benefits accrued is the acceleration of reaction rates, which minimizes reactor volume. Although the backmixing alters the product selectivity such that a lower proportion of the isobutane is converted to tertiary butyl hydroperoxide, the concomitant higher production of tertiary butyl alcohol is valuable and pays for the higher isobutane consumption needed for a given production requirement of tertiary butyl hydroperoxide.

Because oxygen and hydrocarbons are being mixed together, there is the potential hazard of an explosion if there is a vapor phase. For this reason a liquid-full arrangement is adopted. This avoids the creation of a mixture of hydrocarbon and oxygen in a contiguous vapor phase under normal and most abnormal circumstances. Other reactor concepts, such as a boiling liquid-phase design or an all-vapor system lack this inherent protection.

The object of the preferred design is to eliminate equipment with moving parts.

The reactor consists of a vertical, cylindrical pressure vessel with overall dimensions and end closure design determined by least cost considerations for the volume and pressure demanded by the process. Within the vessel is a cylindical baffle of length approximately the same as the vessel straight side length and of diameter such that the inside cross-section area is the same as the annular area between the baffle and pressure vessel wall. At the top of the baffle annulus, cooling coils or plates are arranged which pick up heat from the process liquid irrigating the outside of the cooling surface and transfer it to boiling water within the coils or plates. A sparger is located at the bottom of the reactor whereby oxygen gas is introduced to the reacting mixture. Cold or preheated isobutane liquid feed (as required) is introduced into the annular volume uniformly around the periphery and downwards parallel with and between the vessel wall and baffle plate. Reactor effluent is withdrawn from the highest point of the vessel top closure.

The function of the device relies on the change of density of the reacting liquid with temperature. The annular volume is filled by slightly cooler liquid consisting of a recirculation flow leaving the cooling surface, combined with the injected cold feed. As the reaction proceeds, heat is liberated and the core volume liquid is slightly warmer than the annular liquid as a result. The difference in average liquid density on each side of the baffle plate creates a bouyancy force that drives a natural circulation of liquid up the core and down the annulus. This natural circulation is assisted by the dispersed vapor phase rising through the core from the sparger until the vapor is totally dissolved, and by the liquid feed injection in a downwards direction in the annulus. In fact, the natural circulation without the beneficial effects of feed and vapor injection is sufficient on its own to generate a satisfactory circulation. The magnitude of the circulation is determined by the dynamic equilibrium between the driving bouyancy force and the resisting surface friction force experienced by the flowing liquid. In the present design the flow is substantial and quite sufficient to assure uniformity throughout the reactor volume, and efficient heat transfer in the cooling coils.

In line with the desire to eliminate moving parts from the equipment, the coolant supplied to the cooling surface is driven by conventional thermosyphonic action. This generates the necessary bouyancy forces to drive the coolant flow by partial vaporization of the coolant as it picks up heat from the process liquid. The circulation originates in an elevated vessel (termed a steam drum) and returns to the same vessel which also acts to separate steam from unvaporized water. The unvaporized water rejoins the circulation while steam is released at the vessel top to be used usefully elsewhere in the process. Water coolant inventory is maintained by makeup of suitably treated water, but, should this fail, the water inventory of the steam drum is sufficient to support cooling for a defined period. This period should allow time for an orderly reactor shutdown or for restoration of the water supply. In the patent design it is taken as one hour.

The cooling surface is most appropriately provided in two banks encountered by the circulating process liquid in series, i.e., one is above the other in the annular space. This has an advantage in that, should cooling fail in one of the banks, the process can continue while relying on heat removal in remaining bank. This is possible in the present design simply by reducing the steam drum from steam header pressure (25 psig) to atmosphere (0 psig). This lowers water coolant temperature, doubles the temperature difference between the liquids and thereby allows the single bank to carry the whole duty alone. This is an additional level of safety.

Preparation of Tertiary Butyl Hydroperoxide

In accordance with the present invention, tertiary butyl hydroperoxide is prepared by reacting oxygen with liquid isobutane.

Accordingly, the reaction mixture that continually flows upwardly through the draft tube 14 will normally comprise a mixture of unreacted isobutane, tertiary butyl hydroperoxide, tertiary butyl alcohol and reaction by-products.

Reaction conditions are established in the draft tube 14 in a manner to be described including, in general, a reaction temperature of about 130° to about 160° C., a pressure of about 400 to about 1000 psig and a conversion of about 20 to about 40 wt. % of the isobutane, based on the rate of injection or fresh isobutane feedstock. More preferably, the reaction temperature will be within the range of about 140° to about 150° C., the reaction pressure will be about 500 to about 600 psig and conversion will be within the range of about 20 to about 30 wt. % of the isobutane, based on the rate of injection of fresh isobutane feedstock.

The desired reaction conditions are established by correlating the rate of flow of the circulating reaction mixture with the rate of the injection of oxygen and fresh isobutane feedstock and the rate of withdrawal of reaction mixture.

By way of example, the reaction mixture flowing through the draft tube 14 will comprise of unreacted isobutane, tertiary butyl hydroperoxide, tertiary butyl alcohol and by-products. About 25 wt. % of the reaction mixture will be withdrawn from the reactor through the discharge line 26 and will be replaced by an equivalent amount of fresh isobutane feedstock charged by way of the line 32.

Oxygen is charged to the bottom of the draft tube by way of the line 18, as indicated, in a molar ratio, for example, of about 0.2 mole equivalents of oxygen per mole of isobutane charged to the reactor by the isobutane charge line 32.

In accordance with this embodiment, the temperature of the reaction mixture at the bottom of the draft tube 14 will be decreased at the exit of the cooling coils in the annular space 16.

In accordance with the preferred embodiment of the present invention, the steam release drum 38 is sized so as to contain an inventory of water sufficient to sustain cooling for a predetermined desired period of time in the event that the supply of water to the fresh water feed line 40 should fail for any reason. This time should be sufficient to allow for an orderly reactor shutdown or for the restoration of water from an alternate source. Suitably, the inventory will be such that the water inventory in the steam release drum 38 will provide for at least one hour of cooling without any additional supply of fresh water through the fresh water feed line 40.

As another safety feature, if for any reason, flow of fresh isobutane feed through the line 32 should cease, the amount of cooling achieved in the annular space 16 can be increased by depressuring the steam drum from a desired operating pressure of from about 5 to about 15 psig. to a lower pressure such as atmospheric pressure (0 psig).

Having thus described our invention, what is claimed is:

1. A liquid phase method for the continuous noncatalytic exothermic reaction of isobutane with oxygen to form a reaction mixture comprising unreacted isobutane, tertiary butyl hydroporoxide, tertiary butyl alcohol and by-products which comprises:

a. continuously injecting oxygen into a closed, upstanding thermosyphonic reactor filled with isobutane, said reactor having an updraft section and a downdraft section, said oxygen being injected adjacent the bottom of said updraft section to initiate an exothermic oxidation reaction of the oxygen with isobutane to form a reaction mixture comprising unreacted isobutane, tertiary butyl hydroperoxide, tertiary butyl alcohol and by-products, whereby the temperature of said reaction mixture will increase as said reaction mixture flows upwardly through said updraft section, and whereby the density of said reaction mixture at the top of said updraft section will be less than the density of said reaction mixture adjacent the bottom of said updraft section, b. continuously removing a stream of said reaction product from said reactor adjacent the top of said updraft section an redirecting the flow of the remainder of the said reaction product to the top of said downdraft section, c. continuously endothermically removing heat from said circulating stream of reaction mixture in an endothermic heat exchange zone adjacent the top of said downdraft section and injecting a feed stream of cold fresh isobutane feedstock into said reactor adjacent the top of said downdraft section, whereby the temperature of said reaction mixture adjacent the top of said downdraft section will be lowered, thereby increasing the density of said reaction mixture adjacent the top of said downdraft section, whereby said thus-cooled reaction mixture will flow downwardly through said downflow section to the bottom of said upflow section, and d. adjusting the rate of injection of oxygen into said reactor, the rate of addition of isobutane to said reactor and the rate of withdrawal of reaction product from said reactor in order to establish reaction conditions in the upflow section of said reactor including a temperature within the range of about 130° to about 160° C., a pressure of about 400 to about 1,000 psig and a conversion of about 20 wt. % to about 40 wt. % of the isobutane, based on the rate of injection of fresh isobutane feedstock, e. whereby continuous thermosyphonic circulation of said reaction mixture and continuous mixing of said feed stream with said reaction mixture can be accomplished without the use of externally driven mixers and circulators.

2. A method as in claim 1 wherein the rate of injection of oxygen into said reactor, the rate of addition of isobutane to said reactor and the rate of withdrawal of reaction product from said reactor are adjusted in order to establish reaction conditions in the upflow section of said reactor including a temperature within the range of about 140° to about 150° C., a pressure of about 500 to about 600 psig and a conversion of about 20 wt. % to about 30 wt. % of the isobutane, based on the rate of injection of fresh isobutane feedstock.

3. A method as in claim 1 wherein heat is removed from said hot reaction mixture adjacent the top of said downflow section by bringing said hot reaction mixture into indirect heat exchange contact with water.

4. A liquid phase method for the continuous thermosyponic non-catalytic reaction of isobutane with oxygen in a reaction mixture comprising unreacted isobutane, tertiary butyl hydroperoxide, tertiary butyl alcohol and by-products which comprises:

a. continuously injecting oxygen into the lower portion of a thermosyphonically vertically upwardly circulating stream of a reaction product comprising isobutane, tertiary butyl hydroperoxide, tertiary butyl alcohol and by-products in an oxygen injection zone to exothermally react the oxygen with the isobutane in the oxygen injection zone to increase the temperature of the reaction mixture in the oxygen injection zone and to decrease the density of the reaction mixture in the oxygen injection zone, b. continuously removing a stream of reaction product from the upper portion of said vertically upwardly circulating stream of reaction product, c. continuously injecting a feed stream of cold fresh isobutane into the upper portion of a vertically downwardly flowing thermosyphonically circulating stream, and continuously endothermally removing heat from the upper portion of said thermosyphonically downwardly flowing circulating stream to lower the temperature of the reaction mixture and to increase the density of the reaction mixture in said upper portion of said thermosyphonically downwardly flowing circulating stream, and d. adjusting the rate of injection of oxygen, the rate of addition of isobutane and the rate of withdrawal of reaction product to establish reaction conditions in the oxygen injection zone including a temperature within the range of about 130° to about 160° C., a pressure of about 400 to about 1,000 psig and a conversion of about 20 wt. % to about 4 wt. % of the isobutane, based on the rate of injection of fresh isobutane, e. whereby continuous thermosyphonic circulation of said circulating stream of reaction mixture can be accomplished, whereby continuous mixing said isobutane with said circulating stream of reaction mixture can be accomplished, and whereby continuous mixing of oxygen with said circulating stream of reaction mixture can be accomplished.

5. A liquid phase method for the continuous thermosyponic non-catalytic reaction of isobutane with oxygen in a reaction mixture comprising unreacted isobutane, tertiary butyl hydroperoxide, tertiary butyl alcohol and by-products, said reaction being conducted in a reaction vessel consisting essentially of a vertical tubular reactor having a vertical draft tube mounted therein, said method comprising the steps of:

a. continuously circulating said reaction mixture upwardly through said draft tube and downwardly through the annulus between the draft tube and the reaction wall, b. continuously injecting oxygen into the bottom of the draft tube to exothermally react the oxygen with the isobutane in the draft tube to increase the temperature of the reaction mixture therein and to decrease the density of the reaction mixture therein, c. continuously removing a stream of reaction product from the top of said reaction vessel, d. continuously injecting a feed stream of cold fresh isobutane into said annulus adjacent the top thereof to lower the temperature of the reaction mixture and to increase the density of the reaction mixture in the annulus, and e. adjusting the rate of injection of oxygen, the rate of addition of isobutane and the rate of withdrawal of reaction product to establish reaction conditions in the oxygen injection zone including a temperature within the range of about 130° to about 160° C., a pressure of about 400 to about 1,000 psig and a conversion of about 20 wt. % to about 40 wt. % of the isobutane, based on the rate of injection of fresh isobutane, f. whereby continuous thermosyphonic circulation of said circulating stream of reaction mixture can be accomplished, whereby continuous mixing said isobutane with said circulating stream of reaction mixture can be accomplished, and whereby continuous mixing of oxygen with said circulating stream of reaction mixture can be accomplished.

* * * * *